United States Patent [19]

Kramer et al.

[11] Patent Number: 4,578,068
[45] Date of Patent: Mar. 25, 1986

[54] ABSORBENT LAMINATE STRUCTURE

[75] Inventors: Timothy A. Kramer, Cincinnati; Gerald A. Young, Springfield Township, Hamilton County; Ronald W. Kock, Wyoming, all of Ohio

[73] Assignee: The Procter & Gamble Company, Cincinnati, Ohio

[21] Appl. No.: 563,339

[22] Filed: Dec. 20, 1983

[51] Int. Cl.$^4$ .............................................. A61F 13/16
[52] U.S. Cl. ..................................... 604/368; 428/152; 428/153; 428/154; 428/195; 428/198; 428/206; 428/211; 428/219; 428/283; 428/284; 428/340; 428/402; 428/913
[58] Field of Search ................. 604/368; 428/281, 282, 428/283, 284, 195, 198, 201, 204, 206, 211, 537, 219, 340, 913, 152, 153, 154; 156/183, 209

[56] References Cited

U.S. PATENT DOCUMENTS

| | | |
|---|---|---|
| 2,331,271 | 10/1943 | Gilchrist ............................ 128/284 |
| 2,890,700 | 6/1959 | Lonberg-Holm ................... 128/284 |
| 3,070,095 | 12/1962 | Torr ................................. 128/284 |
| 3,121,427 | 2/1964 | Mosier ............................. 128/284 |
| 3,137,893 | 6/1964 | Gelpke .................................. 18/4 |
| 3,334,789 | 10/1967 | Arnold et al. ..................... 128/287 |
| 3,371,666 | 3/1968 | Lewing ............................ 128/285 |
| 3,381,688 | 5/1968 | Satas ................................ 128/296 |
| 3,528,421 | 9/1970 | Vaillancourt et al. ............. 128/284 |
| 3,654,929 | 4/1972 | Nilsson et al. .................... 128/287 |
| 3,661,154 | 5/1972 | Torr ................................. 128/284 |
| 3,669,103 | 6/1972 | Harper et al. .................... 128/156 |
| 3,670,731 | 6/1972 | Harmon ........................... 128/284 |
| 3,686,024 | 8/1972 | Nankee et al. ................. 117/140 A |
| 3,810,468 | 5/1974 | Harper et al. .................... 128/156 |
| 3,817,827 | 6/1974 | Benz ................................ 156/183 |
| 3,888,256 | 6/1975 | Studinger ........................ 128/284 |
| 3,888,257 | 6/1975 | Cook et al. ....................... 128/296 |
| 3,901,236 | 8/1975 | Assarsson et al. ................ 128/284 |
| 3,903,889 | 9/1975 | Torr ................................. 128/287 |
| 3,959,569 | 5/1976 | Burkholder, Jr. ................. 428/475 |
| 3,971,379 | 7/1976 | Chatterjee ....................... 128/285 |
| 4,055,180 | 10/1977 | Karami ............................ 128/287 |
| 4,055,184 | 10/1977 | Karami ............................ 128/287 |
| 4,102,340 | 7/1978 | Mesek et al. ..................... 128/287 |
| 4,103,062 | 7/1978 | Aberson .......................... 428/283 |
| 4,105,033 | 8/1978 | Chatterjee et al. ............... 128/285 |
| 4,158,594 | 6/1979 | Becker et al. .................... 156/183 |
| 4,217,901 | 8/1980 | Bradstreet et al. ............ 128/290 R |
| 4,224,366 | 9/1980 | McCabe, Jr. ....................... 428/72 |
| 4,232,674 | 11/1980 | Melican .......................... 128/287 |
| 4,235,237 | 11/1980 | Mesek et al. .................... 128/284 |
| 4,260,443 | 4/1981 | Lindsay et al. .................. 156/220 |
| 4,269,188 | 5/1981 | Nishizawa et al. ............... 128/287 |
| 4,293,609 | 10/1981 | Erickson ......................... 428/246 |
| 4,297,410 | 10/1981 | Tsuchiya et al. ................ 428/283 |
| 4,327,728 | 5/1982 | Elias ................................ 128/285 |
| 4,333,463 | 6/1982 | Holtman .......................... 128/287 |
| 4,338,371 | 7/1982 | Dawn et al. ..................... 428/283 |
| 4,341,215 | 7/1982 | Eldridge ........................... 128/285 |
| 4,360,021 | 11/1982 | Stima .............................. 128/287 |
| 4,364,992 | 12/1982 | Ito et al. .......................... 428/283 |
| 4,381,782 | 5/1983 | Mazurak et al. ................. 604/368 |
| 4,381,783 | 5/1983 | Elias ................................ 604/368 |
| 4,392,908 | 7/1983 | Dehnel ............................ 427/194 |
| 4,411,660 | 10/1983 | Dawn et al. ..................... 604/396 |
| 4,414,255 | 11/1983 | Tokuyoma et al. .............. 428/154 |

FOREIGN PATENT DOCUMENTS 108637 5/1984 European Pat. Off. .
2049553 12/1980 United Kingdom .

Primary Examiner—James J. Bell
Attorney, Agent, or Firm—E. Kelly Linman; Milton B. Graff, IV; John V. Gorman

[57] ABSTRACT

The present invention provides a layered absorbent structure, the structure having an upper surface and a lower surface. The structure comprises:
(a) n webs of fibrous material, n being an integer of two or more. The webs are layered such that there is an uppermost web, a lowermost web, $n-2$ intermediate webs, and $n-1$ interfaces of two opposed adjacent contacting surfaces of adjacent webs. Each of the interfaces has a surface area.
(b) Absorbent particles forming a discontinuous layer at one or more of the interfaces.

The opposed adjacent contacting surfaces at each interface where particles are present are substantially entirely frangibly bonded by fiber entanglement between the contacting surfaces. The particles are immobilized at said interface(s) substantially entirely by fiber entrapment.

32 Claims, 14 Drawing Figures

ABSORBENT LAMINATE STRUCTURE

TECHNICAL FIELD

The present invention relates to absorbent structures that may be used as absorbent cores for diapers, catamenial products, bandages, and the like. The present invention relates particularly to such absorbent structures which are a combination of absorbent fibrous material and absorbent particles.

BACKGROUND OF THE INVENTION

Absorbent structures are useful as absorbent cores in a variety of different products, for example, diapers, incontinent pads, catamenial products, bandages, and the like. Such absorbent structures have generally been comprised primarily of absorbent fibrous materials, such as absorbent papers, absorbent cloths, fibrous batts, and the like.

More recently, a new class of compounds commonly known as superabsorbent polymers have been developed and are gaining increasing use as at least a part of absorbent structures. Superabsorbent polymers as used herein are water-insoluble polymeric materials typically capable of absorbing at least fifteen times their weight of water. Such superabsorbent polymers are available in a variety of forms; for example, they may be a film or a particulate form such as flakes, powders, or granules. Superabsorbent polymers generally differ from many conventional absorbent materials in that once an aqueous fluid is absorbed by most superabsorbent polymers, it generally cannot be expressed from the superabsorbent polymer under moderate pressure. This is often highly desirable in an absorbent structure in that it prevents absorbed fluid from being expressed out of the structure.

When most superabsorbent polymers absorb aqueous fluids, they swell substantially, often to double their dry dimensions or more at saturation. As most superabsorbent polymers absorb fluid and swell, they generally become a gelatinous mass. If the superabsorbent polymer is in a particulate form and the particles are close to one another, they can coalesce and form a gel barrier which can block the flow of fluid.

Absorbent structures which are combinations of absorbent fibrous materials and superabsorbent polymers are well known. Because the superabsorbent polymer is generally present in such a structure in some particulate form, the fibrous material is used to hold the superabsorbent polymer particles within the absorbent structure.

Absorbent structures are known where superabsorbent polymer particles and absorbent fibers are blended to produce an absorbent structure with the superabsorbent particles dispersed throughout the structure. Such absorbent structures are disclosed in U.S. Pat. Nos. 3,661,154 issued to Torr on May 9, 1972, and 3,888,257 issued to Cook & Jackson on June 10, 1975.

More often absorbent structures which combine absorbent fibrous materials and superabsorbent polymers are constructed such that there are one or more layers of each of the two materials. Such layered absorbent structures are disclosed in U.S. Pat. Nos. 3,070,095 issued to Torr on Dec. 25, 1962; 3,371,666 issued to Lewing on Mar. 5, 1968; 3,381,688 issued to Satas on May 7, 1968; 3,654,929 issued to Nilsson, Udden & Wennerblom on Apr. 11, 1972; 3,669,103 issued to Harper, Bashaw & Atkins on June 13, 1972; 3,670,731 issued to Harmon on June 20, 1972; 3,888,256 issued to Studinger on June 10, 1975; 3,901,236 issued to Assarsson, Kling & Yen on Aug. 26, 1975; 3,959,569 issued to Burkholder on May 25, 1976; 4,055,180 and 4,055,184 both issued to Karami on Oct. 25, 1977; 4,102,340 issued to Mesek & Repke on July 25, 1978; 4,103,062 issued to Aberson & Stulgate on July 25, 1978; 4,105,033 issued to Chatterjee & Morbey on Aug. 8, 1978; 4,232,674 issued to Melican on Nov. 11, 1980; 4,260,443 issued to Lindsay, Meintrup & Slawny on Apr. 7, 1981; 4,269,188 issued to Nishizawa, Shirose & Itoh on May 26, 1981; 4,293,609 issued to Erickson on Oct. 6, 1981; and 4,360,021 issued to Stima on Nov. 23, 1982. Such a layered absorbent structure is also disclosed in U.K. Patent Application No. 2,049,553 published on Dec. 31, 1980.

For absorbent structures where absorbent fibrous materials and superabsorbent polymer particles are present in layers, a number of techniques have been used to secure the superabsorbent polymer particles within the absorbent structure. Torr '095 discloses sifting superabsorbent particles onto a tissue layer and using flat pressure rollers to press the particles into the tissue. Harper, Bashaw & Atkins discloses layering superabsorbent polymer particles between layers of crepe paper and quilting the structure to hold the particles in place. Harmon discloses securing superabsorbent polymer particles in embossed cavities of paper layers and using an adhesive to secure the layers of paper together. Assarsson, Kling & Yen discloses superabsorbent particles layered between fluff pads which are embossed with a diamond grid pattern. Burkholder discloses superabsorbent polymer particles distributed between layers of tissue, contacting the layered structure with steam to make the particles sticky, and compressing the structure to adhere the particles to the tissue layers. Karami '180 discloses a structure having superabsorbent polymer particles in pockets between a cellulose sheet and a polyethylene film which are adhered around the pockets by adhesive or heat sealing. Aberson & Stulgate discloses a densified bonded layer of fluff pulp and superabsorbent polymer particles which is compressed and heated to fix the particles to the fluff fibers. Melican discloses depositing superabsorbent polymer particles in a predetermined pattern between wetted tissue layers and compressing the resulting structure to adhere the layers together. Lindsay, Meintrup & Slawny discloses layering superabsorbent polymer particles between tissue layers where water is applied at spaced points on the tissue and the layered sheets are embossed to provide points of adhesion such that the particles act as an adhesive between the layers. Stima discloses an absorbent structure having superabsorbent polymer particles in pockets between tissue layers, the tissue layers being adhered by moistening and compressing around the pockets with a grid pattern that matches the pockets. U.K. Patent Application No. 2,049,553 discloses an absorbent structure having superabsorbent polymer particles between two sheets which are adhered by dry embossing between a textured roll and a flat roll such that some areas of the resulting layered structure are highly compressed while other areas are not compressed at all.

It has been found that the absorbent structures disclosed in the above references suffer from one or more of the following disadvantages:

(1) the full absorbent rate and/or capacity of the superabsorbent particles are not capable of being utilized due to physical restraint of the particles or changes in the absorptive rate and/or capacity of the particles caused by the process of making the structure;

(2) fluid is not readily dispersed through the structure or around the particles; consequently, optimum contact between the fluid to be absorbed and the superabsorbent polymer particles is not achieved;

(3) the structure cannot be produced such that it is economically attractive.

SUMMARY OF THE INVENTION

It is an object of the present invention to provide a layered absorbent structure containing absorbent particles, preferably superabsorbent polymer particles, where, when the structure is wetted, the particles are free to absorb fluid and swell substantially the same as if they were unconstrained.

It is a further object of the present invention to provide such a structure where fluid contact of the absorbent particles is maximized when the structure is wetted.

It is a still further object of the present invention to provide such a structure where the absorbent particles are separated sufficiently to avoid substantial restriction of fluid flow within the structure due to gel blockage within the structure when it is wetted.

It is a further object of the present invention to provide such a structure where the absorbent particles are substantially immobilized within the structure to avoid shifting of the particles.

It is also an object of the present invention to provide such a structure having sufficient temporary void capacity to handle sudden gushes of fluid.

It is a further object of the present invention to provide such a structure where fluid to be absorbed is rapidly wicked to the absorbent particles.

It is also an object of the present invention to provide a process for producing such a layered absorbent structure.

It is a further object of the present invention to provide such a process which does not adversely affect the absorbent rate or capacity of the absorbent particles.

The present invention provides a layered absorbent structure having an upper surface and a lower surface. The structure comprises:

(a) n webs of fibrous material, n being an integer of two or more. Each of the webs has two substantially parallel surfaces. The webs are layered such that there is an uppermost web, a lowermost web, n−2 intermediate webs, and n−1 interfaces of two opposed adjacent contacting surfaces of adjacent webs. Each of the interfaces has a surface area.

(b) Absorbent particles which form a discontinuous layer at one or more of the interfaces.

The opposed adjacent contacting surfaces at each interface where the particles are present are frangibly bonded substantially entirely by fiber entanglement between the contacting surfaces. The particles are immobilized at the interface(s) substantially entirely by fiber entrapment.

DETAILED DESCRIPTION OF THE INVENTION

Products of the present invention include layered absorbent structures comprising layers of webs of fibrous materials and fluid absorbent swellable particles, preferably superabsorbent polymer particles.

As used herein a web of fibrous material is a sheet of thin, substantially contiguous material having two substantially parallel surfaces. Although a web of fibrous material as used herein need not be flat or smooth, it is or can be laid out in a substantially planar, two-dimensional arrangement of indefinite length and indefinite width projecting in these two dimensions. The direction perpendicular to this substantially planar, two-dimensional arrangement of a web of material will be referred to herein as the z-direction of the web of material. The z-direction structure of the webs of fibrous materials is an important attribute of the preferred layered absorbent structures of the present invention.

A web of fibrous material as used herein may be considered to have a true thickness and an apparent thickness. The true thickness of such a web of fibrous material is the distance between its two substantially parallel surfaces. Because the webs are of fibrous materials, the microscopic surfaces of the webs of materials are very irregular. Therefore, when the surfaces of these webs are described as substantially planar, the webs are being viewed on a macroscopic scale. The surfaces of the webs are also described as substantially parallel; this does not mean that the webs cannot have thick and thin areas and even some discontinuous areas (e.g., holes). Instead, substantially parallel surfaces, as used herein, means that when there is a substantial macroscopic change of direction of one surface of a web of fibrous material, the other surface of the web makes a substantially parallel change of direction. Preferred webs of fibrous materials of layered absorbent structures of the present invention have such macroscopic changes of direction of the surface of the web in the form of protrusions and concavities in the webs. The apparent thickness of such webs is a measure of the distance between protrusion peaks on opposed surfaces of the webs, or between protrusion peaks on one surface and the general plane of the other surface if only the one surface has protrusion peaks.

Examples of webs of fibrous materials used in the absorbent structures of the present invention include many papers and nonwoven materials. The webs of fibrous materials used in the present invention are preferably webs of absorbent materials, more preferably webs of absorbent papers, more preferably still webs of absorbent tissues. The webs of fibrous materials of a layered absorbent structure of the present invention may all be the same fibrous material or may be different fibrous materials.

The preferred webs of absorbent tissue of a layered absorbent structure of the present invention each preferably has a basis weight of from about 10 $g/m^2$ to about 100 $g/m^2$, more preferably from about 15 $g/m^2$ to about 40 $g/m^2$.

The absorbent particles used in the layered absorbent structures of the present invention may be any fluid absorbent material that swells when it absorbs fluid. It is highly preferred that the absorbent particles be water-insoluble polymeric materials (superabsorbent polymers) having a water absorption capacity of 15 times their dry weight or more, preferably having a water absorption capacity of 30 times their dry weight or more, more preferably having an aqueous saline solution absorption capacity of 30 times their dry weight or more of a solution of 1% sodium chloride in water.

There is a wide variety of materials which are or can be physically structured to perform as superabsorbent polymers. Although the following list is not meant to be inclusive of all superabsorbent polymers, such materials are disclosed in the following U.S. Pat. Nos.: 2,798,053 issued to Brown on July 2, 1957; 2,988,539 issued to Cohen, Spaulding & Jones on June 13, 1961; 3,220,960 issued to Wichterle & Lim on Nov. 30, 1965; 3,247,171 issued to Walker & Pillepich on Apr. 19, 1966; 3,393,168 issued to Johnson on July 16, 1968; 3,419,006 issued to King on Dec. 3, 1968; 3,425,971 issued to Gugliemelli, Weaver & Russell on Feb. 4, 1969; 3,514,419 issued to Darlow & Gibb on May 26, 1970; 3,628,534 issued to Donohue on Dec. 21, 1971; 3,661,815 issued to Smith on May 9, 1972; 3,664,343 issued to Assarsson on May 23, 1972; 3,669,103 issued to Harper, Bashaw & Atkins on June 13, 1972; 3,670,731 issued to Harmon on June 20, 1972; 3,783,872 issued to King on Jan. 8, 1974; 3,810,468 issued to Harper, Bashaw & Atkins on May 14, 1974; 3,926,891 issued to Gross & McFadden on Dec. 16, 1975; 3,935,099 issued to Weaver, Bagley, Fanta & Doane on Jan. 27, 1976; 3,954,721 issued to Gross on May 4, 1976; 3,971,379 issued to Chatterjee on July 27, 1976; 3,980,663 issued to Gross on Sept. 14, 1976; 3,993,553 issued to Assarsson & King on Nov. 23, 1976; 3,997,484 issued to Weaver, Bagley, Fanta & Doane on Dec. 14, 1976; 4,017,653 issued to Gross on Apr. 12, 1977; 4,018,951 issued to Gross on Apr. 19, 1977; 4,044,766 issued to Kaczmarzyk, Hlaban & Bernardin on Aug. 30, 1977; 4,045,387 issued to Fanta & Doane on Aug. 30, 1977; 4,051,086 issued to Reid on Sept. 27, 1977; 4,058,124 issued to Yen & Osterholtz on Nov. 15, 1977; 4,076,673 issued to Burkholder, Jr. on Feb. 28, 1978; 4,090,013 issued to Ganslaw & Katz on May 16, 1978; 4,093,776 issued to Aoki & Yamasaki on June 6, 1978; 4,102,340 issued to Mesek & Repke on July 25, 1978; 4,105,033 issued to Chatterjee & Morbey on Aug. 8, 1978; 4,117,184 issued to Erickson & Krajewski on Sept. 26, 1978; 4,190,562 issued to Westerman on Feb. 26, 1980; 4,200,557 issued to Chatterjee & Schwenker, Jr. on Apr. 29, 1980; and 4,232,674 issued to Melican on Nov. 11, 1980.

The superabsorbent polymers preferred for use in the layered absorbent structures of the present invention comprise saponified starch-polyacrylonitrile graft copolymers, starch-polyacrylic acid graft copolymers, crosslinked/grafted cellulose, saponified vinyl acetate-acrylic acid copolymers, starch grafted polyvinyl acetate, acrylic acid polymers, crosslinked polyethylene oxide, and the like. The superabsorbent polymer particles used in such structures may all be the same or a mixture of different superabsorbent polymers.

Absorbent particles are incorporated in the layered absorbent structures of the present invention in particulate form as a discontinuous layer between webs of fibrous materials. The absorbent particles may be in a form such as flakes, powders, or granules. The preferred superabsorbent polymer particles used in the present invention are flakes or granules. It is preferable to minimize the amount of absorbent particles that can substantially shift position in or escape from the absorbent structure. Therefore, the particles are preferably larger than the openings of the fibrous webs. For absorbent structures where preferred absorbent tissues are used as the webs of fibrous materials, it is preferred that the size distribution of the particles be such that about 90% (by weight) or more of the particles comprise two perpendicular dimensions of from about 0.05 mm to about 1.0 mm, more preferably such that about 70% (by weight) or more of the particles comprise two perpendicular dimensions of from about 0.15 mm to about 0.6 mm.

A layered absorbent structure of the present invention has an upper surface and a lower surface. The structure comprises n webs of fibrous materials, n being an integer of two or more. The webs are layered such that there is an uppermost web, a lowermost web, $n-2$ intermediate webs, and $n-1$ interfaces of two opposed adjacent contacting surfaces of adjacent webs. Each of the interfaces has a surface area. Absorbent particles form a discontinuous layer at one or more of the interfaces.

Many absorbent structures disclosed in the references cited hereinbefore are comprised of layered webs of fibrous materials with superabsorbent polymer particles between the web layers. One reason the superabsorbent particles are incorporated in such structures is because they have a greater water absorbing capacity per gram than conventional absorbent fibrous materials. Because of this greater absorbing capacity of the superabsorbent polymer particles, such absorbent structures can be made thinner, less bulky, and lighter in weight than absorbent structures made entirely from conventional absorbent fibrous materials. Such thinner, less bulky, lighter weight absorbent structures provide potential benefits when incorporated in products such as disposable diapers, disposable incontinent briefs, sanitary napkins, absorbent bandages, and the like.

For such absorbent products, the absorbing capacity of the product is a primary concern. However, the rate of absorption of fluid is also generally of importance for such products. Disposable diapers, incontinent briefs, and catamenial products, in particular, must be capable of handling gushes of fluid in short periods of time. In the layered absorbent structures of the present invention, a primary function of the webs of fibrous materials is to absorb the gushes of fluid and to transport the fluid to the superabsorbent polymer particles for absorption by them. Thus the webs of fibrous materials preferably have sufficient void volume to handle such gushes of fluid and good wicking properties to quickly disperse the fluid throughout the absorbent structure and to the absorbent particles. Absorption of the fluid from the fibrous material by the superabsorbent polymer particles regenerates the absorbing capacity of the fibrous material so that it is capable of absorbing other gushes of fluid.

A rapid absorption of the fluid by the superabsorbent particles is desirable. The rate of absorption of fluid by the particles is, of course, dependent on the superabsorbent polymer employed; however, it is also dependent on the physical attributes of the particles and their relationship to the webs of fibrous materials. The rate of absorption of fluid by such a particle is proportional to the surface area of the particle exposed to the fluid being absorbed. Therefore, a maximum absorption rate is achieved by the particle when it is surrounded by the fluid being absorbed. This can be accomplished in layered absorbent structures of the present invention if each particle is surrounded by the fibrous material which transports the fluid to the particle.

As superabsorbent polymer particles absorb fluid, they swell substantially. Such a particle will exhibit its maximum rate of absorption and maximum absorbing capacity if it is free-floating, totally unconstrained in the fluid being absorbed. If such particles are constrained such that they are not free to swell in an uninhibited manner, either the rate of absorption of fluid by the particle, or the capacity of the particle to absorb fluid, or both, will be adversely affected. The absorption rate and/or capacity of many commercially available superabsorbent polymer particles are adversely affected by process conditions which affect their structure, particularly those involving wetting and drying, excessive heating, excessive pressure, or direct contact with adhesives. Such process steps, particularly those involving wetting and drying of the particles, can also increase the cost of making layered absorbent structures. It has been found that the prior art layered absorbent structures disclosed in the references cited hereinbefore all have either the rate of absorption of fluid by the superabsorbent polymer particles, or the absorbing capacity of the particles, or both, inhibited in one or more ways.

If the superabsorbent polymer particles in an absorbent structure are constrained such that they are in contact with one another, both the rate of absorption and absorption capacity of the particles will be adversely effected. Since the particles are in contact, fluid cannot totally surround each particle and its maximum rate of absorption cannot be achieved. As the contacting particles absorb fluid and begin to swell, they are not free to swell to their fullest extent because of their contact with one another; thus they are unable to achieve their maximum absorbing capacity. Also, as such particles in contact absorb water and swell, they often will coalesce to form a gel layer which may block the flow of fluid to other particles, thus reducing the absorption rate and capacity of the structure as a whole. It is therefore preferable to have the superabsorbent polymer particles separated within a layered absorbent structure with sufficient spacing between the particles to allow them to swell to the maximum size without contacting neighboring particles.

Several of the references cited hereinbefore disclose layered absorbent structures where superabsorbent particles are clustered together such that their rate of absorption and absorption capacity would be inhibited. In Harper, Bashaw & Atkins '103, Assarsson, King & Yen, Karami '180, Lindsay, Meintrup & Slawny, and Stima, superabsorbent particles are held between absorbent paper layers in pockets formed by quilting, embossing, or other means. In Torr '095, Nilsson, Udden & Wennerblom, and Studinger, the superabsorbent polymer particles are not only in contact, but constitute a substantially continuous layer such that when they absorb water and swell they will form a gel layer which will block the flow of fluid through the absorbent structure.

If the fibrous materials rigidly constrain the superabsorbent polymer particles in an absorbent structure, swelling of the particles will be inhibited and their absorption capacity, and possibly their rate of absorption, will be adversely effected. However, if the particles are not held stationary by the fibrous materials, the particles will be able to move within the structure and their desired separation will not be maintained. It is therefore preferable, in a layered absorbent structure where the particles are at the interfaces between webs of fibrous materials, to have the opposed adjacent contacting surfaces of adjacent webs of fibrous materials frangibly bonded to one another at each interface where superabsorbent polymer particles are present, such that the particles are not free to move in the absorbent structure but are free to absorb fluid and swell substantially as if they were unconstrained.

Several of the references cited hereinbefore disclose layered absorbent structures where swelling of the particles would be inhibited due to their being held tightly in the structure by webs of fibrous material. In Harmon, adhesive is used to secure layers of paper together to hold the particles in place. Permanent adhesive bonds between the webs of fibrous materials would not provide frangible bonds between the webs such that the webs can part and allow substantially free expansion of the particles as they swell. U.K. Patent Application No. 2,049,553 discloses a layered absorbent structure having superabsorbent polymer particles between two webs of absorbent paper which are adhered by dry embossing with one highly textured roll and one flat roll. This results in a structure having some highly compacted areas and some areas which are not compacted at all. In the highly compacted areas, the superabsorbent polymer particles would be held tightly within the compacted fibrous structure and would not be free to swell unconstrained. Also, in the uncompacted areas, the particles would be free to move between the paper layers such that they could collect together.

For many commercially available superabsorbent polymer particles, it has been found that if the particles are wetted and redried, the rate of absorption is decreased. This reduced rate of absorption is believed to occur because the wetting, partial swelling, and redrying results in particles having reduced surface area compared to the unwetted particles. Also, if such particles are exposed to excessive heat and/or pressure (which generally results in heating the particles), their absorbing capacity and/or rate of absorption are decreased. Excessive heat is believed to cause crosslinking and/or degradation of the polymer resulting in lower absorbing capacity and lower rate of absorption of the particles. It is therefore preferable to produce layered absorbent structures by methods in which such processing conditions are avoided.

Several of the references cited hereinbefore disclose processes for producing layered absorbent structures in which the superabsorbent particles are exposed to conditions which will reduce their rate of absorption and/or absorbing capacity. Burkholder '569, Karami '184, Melican, and Lindsay, Meintrup & Slawny all disclose processes for producing layered absorbent structures where the superabsorbent particles are exposed to moisture and subsequently dried; the absorbent properties of the particles would be expected to be adversely affected by these processes. Aberson & Stulgate discloses a process for producing layered absorbent structures in which the structure is compressed and heated to fix the particles to the fibers of an absorbent layer; this process would also be expected to adversely affect the absorbent properties of the particles.

In absorbent structures of the present invention, the webs of fibrous materials are preferably frangibly bonded substantially entirely by fiber entanglement between contacting surfaces of adjacent webs at interfaces where absorbent particles are present. The absorbent particles are preferably immobilized at the interfaces substantially entirely by fiber entrapment. The adjacent contacting webs of materials must be sufficiently bonded to one another to provide sufficient integrity for the absorbent structure and to hold the absorbent particles in place and substantially separate from one another in the structure. But at the same time the contacting webs of fibrous materials must be frangibly bonded so that as the particles absorb fluid and swell, the bonds between the contacting webs near such swelling particle will easily be broken such that the adjacent webs in the local area around the swelling particle will separate and allow the particle to swell substantially as if it were unconstrained.

It has been found that frangible bonds can be achieved between adjacent contacting surfaces of adjacent webs of fibrous materials substantially entirely by fiber entanglement between the contacting surfaces by employing certain processes which impart a shearing action between such contacting surfaces of adjacent webs. One example of such a process is the compression of layered webs of fibrous materials in the nip of smooth compression rolls where there is a differential speed between the two rolls. The differential speed between the rolls provides a shearing action in the nip which results in fiber entanglement between the contacting surfaces of the layered webs of fibrous materials. Although the desired frangible bonding between adjacent webs of fibrous materials can be achieved by such a process, it is often difficult to achieve sufficient fiber entanglement between the contacting surfaces of adjacent webs to provide sufficient integrity for the absorbent structure without causing substantial tearing of the webs of fibrous materials.

A preferred method for achieving adjacent contacting webs of fibrous materials which are frangibly bonded substantially entirely by fiber entanglement between the contacting surfaces is by imparting a z-direction structure to the adjacent webs. This is preferably accomplished by feeding adjacent contacting webs of fibrous materials through the nip of rolls having mating z-direction protrusions and concavities. As layered webs of fibrous materials are fed between such rolls, the webs are distorted and the contacting surfaces of the webs undergo somewhat of a shearing action. Such a process preferably results in permanent z-direction protrusions and concavities in the layered webs of fibrous materials. As a result, the interfaces of the contacting surfaces of adjacent webs are no longer substantially entirely parallel to the general planes of the webs. In order to peel webs apart of which such z-direction structure has been imparted, portions of the contacting surfaces of the webs at the interfaces must now slide across one another. The fiber entanglement between the surfaces provides a much more effective bond between the surfaces when they must be slid across one another to separate them than when they are simply pulled in a direction perpendicular to the interface between the contacting surfaces.

Figure 1:
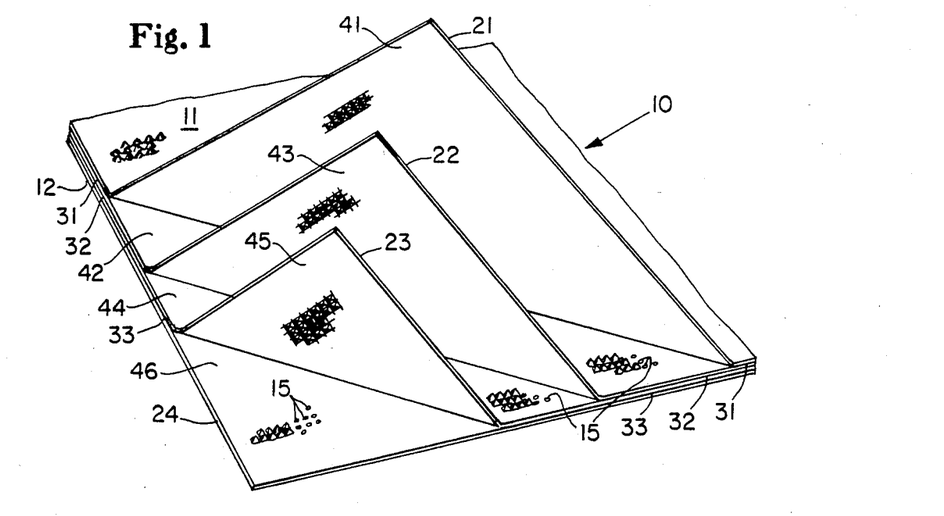
FIG. 1 is a fragmentary, partially delaminated, schematic perspective view of a layered absorbent structure of the present invention.
Figure 2:
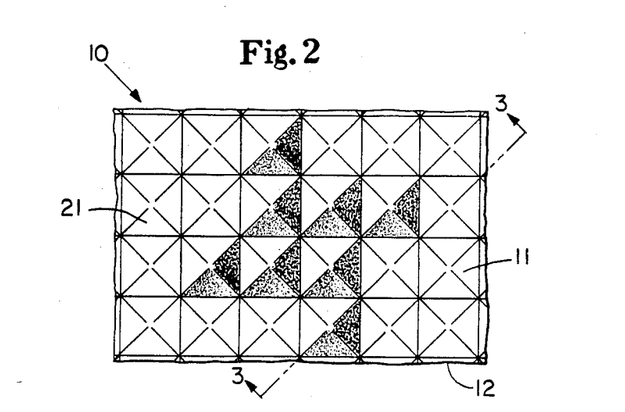
FIG. 2 is a fragmentary, enlarged, schematic plan view of the layered absorbent structure of FIG. 1.
Figure 3:
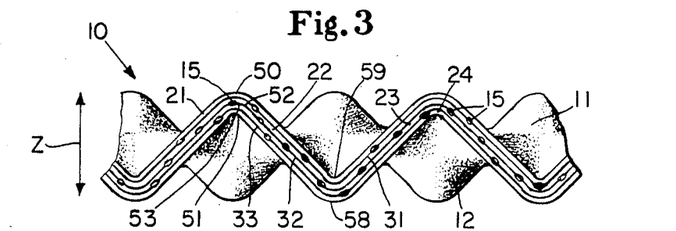
FIG. 3 is a fragmentary, enlarged, cross-sectional, schematic elevation view of the layered absorbent structure of FIG. 2 taken along Line 3—3.

A preferred example of a layered absorbent structure of the present invention is shown in FIG. 1. FIG. 1 is a fragmentary, schematic perspective view of layered absorbent structure 10; it is shown partially delaminated in order to expose the construction of structure 10. FIG. 2 is a fragmentary, enlarged, schematic plan view of layered absorbent structure 10 of FIG. 1, and FIG. 3 is a fragmentary, enlarged, cross-sectional, schematic elevation view of layered absorbent structure 10 taken along line 3—3 in FIG. 2. Layered absorbent structure 10 has upper surface 11 and lower surface 12. Layered absorbent structure 10 comprises four webs of absorbent tissue: uppermost web 21, lowermost web 24, and intermediate webs 22 and 23. There is an interface of two opposed adjacent contacting surfaces between each pair of adjacent webs. For adjacent webs 21 and 22, there is interface 31 of opposed adjacent contacting surfaces 41 of web 21 and 42 of web 22. For adjacent webs 22 and 23, there is interface 32 of opposed adjacent contacting surfaces 43 of web 22 and 44 of web 23. For adjacent webs 23 and 24, there is interface 33 of opposed adjacent contacting surfaces 45 of web 23 and 46 of web 24.

For layered absorbent structures of the present invention, absorbent particles form a discontinuous layer at one or more of the interfaces between adjacent webs. For layered absorbent structure 10, superabsorbent polymer particles 15 are present at each of interfaces 31, 32 and 33. Particles 15 are preferably substantially uniformly distributed at each of interfaces 31, 32 and 33. Particles 15 are preferably spaced sufficiently such that if layered absorbent structure 10 is subsequently wetted by a fluid such that particles 15 absorb the fluid and swell to saturation, the saturated particles would cover less than 100% of the surface area of each of interfaces 31, 32 and 33; more preferably the saturated particles would cover less than 90% of the surface area of each of interfaces 31, 32 and 33. Such a dispersed spacing of absorbent particles is preferred in layered absorbent structures of the present invention to ensure that even when the absorbent particles are saturated with fluid and swollen, there is still room between the swollen particles for fluid to pass through all the layers of the absorbent structure. This enables fluid to freely transport through such absorbent structures until it contacts and is absorbed by absorbent particles which are unsaturated.

Many superabsorbent polymer particles swell such that their dimensions when saturated with fluid are double or more their dry dimensions. Therefore, it is preferred that such dry particles cover no more than 50% of the surface area of each of interfaces 31, 32 and 33; more preferably the particles cover no more than 20% of the surface area of each of interfaces 31, 32 and 33.

Layered absorbent structure 10 is shown in fragmentary, enlarged, schematic plan view in FIG. 2. Layered absorbent structures of the present invention can be laid out in substantially planar, two-dimensional arrangements. Such structures have indefinite lengths and widths projecting in these two dimensions. Layered absorbent structure 10 is laid out in such a manner in FIG. 2; the indefinite lengths and widths of absorbent structure 10 are projecting in the plane of the figure. The direction perpendicular to this substantially planar, two-dimensional arrangement of layered absorbent structure 10 is referred to herein as the z-direction of structure 10. FIG. 3 is a schematic cross-sectional view of absorbent structure 10 taken along line 3—3 of FIG. 2. The z-direction structure of layered absorbent structure 10 is thus shown in FIG. 3, the z-direction being the vertical direction in FIG. 3.

For preferred layered absorbent structures of the present invention, each of the webs of fibrous material has multiple z-direction protrusions in one or both of its surfaces; each such protrusion has a corresponding z-direction concavity in the outer surface of the web. At each interface between layered adjacent webs, each z-direction protrusion of an adjacent surface of a web of fibrous material intermeshes with a concavity of its opposed adjacent surface of its adjacent web. This results in the layered absorbent structure having multiple z-direction protrusions in one or both of its surfaces, each such protrusion having a corresponding z-direction concavity in the other surface of the structure. This can be seen schematically for layered absorbent structure 10 in FIG. 3. Layered absorbent structure 10 has, for example, z-direction protrusion 50 in upper surface 11 and corresponding z-direction concavity 51 in lower surface 12. Each of webs 21, 22, 23 and 24 has a corresponding z-direction protrusion in its upper surface and a z-direction concavity in its lower surface. At each interface, each z-direction protrusion of an adjacent surface intermeshes with a concavity of its opposed adjacent surface. For example, at interface 32, web 23 has a z-direction protrusion 52 in its upper surface 44 which for interface 32 is the adjacent surface of web 23. There is corresponding z-direction concavity 53 in lower surface 43 of web 22 which is the opposed adjacent surface to surface 44 of web 23 at interface 32. Intermeshing protrusion 52 and concavity 53 are preferably frangibly bonded substantially entirely by fiber entanglement.

Layered absorbent structure 10 has z-direction protrusions and concavities in both surfaces; for example, z-direction protrusion 58 is in lower surface 12 and corresponding z-direction concavity 59 is in upper surface 11.

Figure 4:
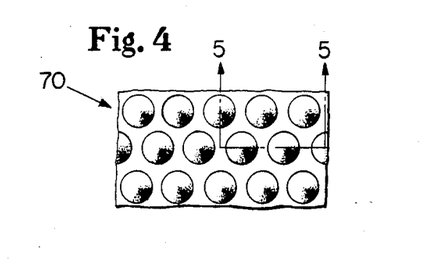
FIG. 4 is a fragmentary, enlarged, schematic plan view of another layered absorbent structure of the present invention.
Figure 5:
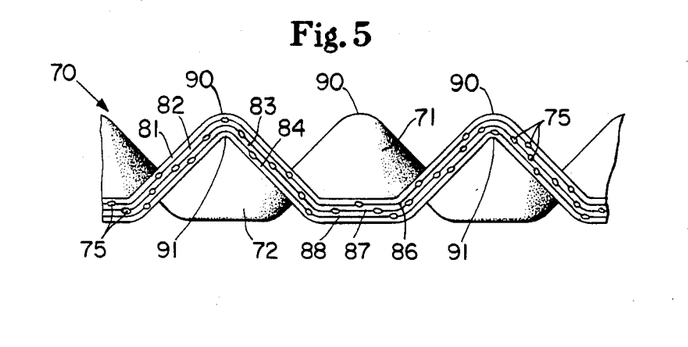
FIG. 5 is a fragmentary, enlarged, cross-sectional, schematic elevation view of the layered absorbent structure of FIG. 4 taken along Line 5—5.

FIGS. 4 and 5 show another layered absorbent structure 70 of the present invention; FIG. 4 is a fragmentary, enlarged, schematic plan view of structure 70, and FIG. 5 is a fragmentary, enlarged, cross-sectional, schematic elevation view of structure 70 taken along line 5—5 of FIG. 4. Layered absorbent structure 70 comprises four webs of absorbent tissue: uppermost web 81, lowermost web 84, and intermediate webs 82 and 83. Layered absorbent structure 70 has interfaces 86, 87 and 88 between adjacent webs with superabsorbent polymer particles 75 forming a discontinuous layer at each of interfaces 86, 87 and 88. Layered absorbent structure 70 has conical protrusions 90 in upper surface 71 and corresponding conical concavities 91 in lower surface 72.

For layered absorbent structures of the present invention where superabsorbent polymer particles are present at interfaces of adjacent webs of fibrous materials, it is preferable that the opposed adjacent surfaces of the adjacent webs at such interfaces are frangibly bonded substantially entirely due to the intermeshing of the z-direction protrusions with the z-direction concavities of the opposed adjacent surfaces. It is also preferable that such opposed adjacent surfaces of adjacent webs at such interfaces where particles are present are substantially entirely in contact over the surface area of the interface except where the particles are present between the opposed adjacent surfaces; in this way, the particles are preferably immobilized substantially entirely by fiber entrapment while the absorbent structure is dry. The particles are preferably distributed substantially uniformly at the interfaces between the webs of materials over all parts of the protrusions and concavities, not clustered at the bottoms of concavities.

Thus, for example, at interface 32 of layered absorbent structure 10 opposed adjacent surfaces 43 of web 22 and 44 of web 23 are frangibly bonded substantially entirely due to the intermeshing of the z-direction protrusions and z-direction concavities of surface 43 of web 22 and surface 44 of web 23. It is believed that their frangible bonding is achieved substantially entirely by fiber entanglement between contacting surfaces 44 and 43.

The integrity of layered absorbent structure 10 is achieved substantially entirely by fiber entanglement between the contacting surfaces of the adjacent webs 21, 22, 23 and 24. In order to separate any two adjacent webs of absorbent structure 10, for example webs 22 and 23, they must be peeled apart in a direction substantially parallel to the z-direction. The fiber entanglement between adjacent surfaces 44 and 43 of webs 22 and 23 respectively, is more effective at preventing separation of the contacting surfaces where the interface 32 is closer to being parallel to the z-direction rather than perpendicular to the z-direction. This is due to the fact that in order to separate in the z-direction, the closer surfaces 44 and 43 are to be parallel to the z-direction, the more they must be slid across one another in order to be separated. Fiber entanglement between surfaces 44 and 43 is more difficult to break when the surfaces are being pulled parallel to one another rather than perpendicular to one another.

Surface 43 of web 22 and surface 44 of web 23 are substantially entirely in contact over the entire surface area of interface 32 except where particles 15 are between these opposed adjacent surfaces 43 and 44. Because opposed adjacent surfaces 43 and 44 are substantially entirely in contact over the surface area of interface 32 except where particles 15 are present between surfaces 43 and 44, particles 15 are immobilized in structure 10 substantially entirely by entrapment by fibers of opposed adjacent surfaces 43 and 44. Particles 15 are preferably substantially dry and are preferably maintained dry until the absorbent structure is used.

Because of the frangible bonds between opposed adjacent surfaces 43 and 44, if absorbent structure 10 is subsequently wetted by a fluid such that particles 15 absorb the fluid and swell, particles 15 are able to swell and become substantially saturated with fluid without substantial constraint of such swelling by the entrapping fibers which immobilize particles 15 when absorbent structure 10 is dry. The pressure exerted on surfaces 43 and 44 by a swelling particle is sufficient to break the frangible bonds between surfaces 43 and 44 in the vicinity of the particle to allow the particle to swell substantially as if it were unconstrained.

Layered absorbent structure 10 thus provides the following highly desired attributes: superabsorbent polymer particles 15 are substantially separated and spaced and surrounded by absorbent fibrous material, so that a fluid to be absorbed can be readily transported to substantially the entire surface area of the particles, and the fluid can substantially completely surround the particles, so that maximum absorption rate and maximum absorbing capacity of the fluid by the particles is achieved; the particles are entrapped within layered absorbent structure 10 such that they will remain so spaced, but the bonds holding webs of absorbent tissues 21, 22, 23 and 24 together are frangible so that when fluid contacts particles 15 and they swell, particles 15 are not substantially constricted but are free to swell without substantial constraint of swelling by webs 21, 22, 23 and 24.

Then absorbent structures of the present invention are utilized in products such as disposable diapers, catamenial devices, bandages, and the like, the frangible bonding between adjacent webs of fibrous materials is preferably sufficient to withstand a reasonable amount of mechanical movement, flexing, and pressure such that the superabsorbent polymer particles remain entrapped and substantially separated between the webs of fibrous materials.

For preferred layered absorbent structures having discrete protrusions and concavities such as those structures shown in FIGS. 2 and 4, it has been found that the bonding between opposed adjacent surfaces of adjacent webs will usually be sufficient when there are from about 10 to about 50 protrusion per square centimeter in one or both of the surfaces of the layered absorbent structure and in each of the corresponding webs, if the protrusions are of sufficient size.

Layered absorbent structures of the present invention may have from two to a large number of webs of fibrous material. The number of webs is generally limited by the thickness of the webs and the ability to impart the desired meshing z-direction protrusions and concavities to a multi-layer stack of such webs. It is preferred that there be from about two to about 12 webs of fibrous material; it is more preferred that there be from about two to about 5 webs of fibrous material. The superabsorbent particles may be provided between each adjacent web of fibrous material as shown in layered absorbent structures 10 and 70; however, the superabsorbent particles may be included between only some of the adjacent webs of fibrous material.

Layered superabsorbent structures of the present invention can be produced comprising the following components: n substantially planar webs of fibrous materials, each of the webs having two substantially parallel surfaces, n being an integer of two or more; and absorbent particles, preferably superabsorbent polymer particles. A preferred process for producing layered absorbent structures of the present invention comprises the following steps. The webs of fibrous materials are layered in substantially planar contact such that there is an uppermost web, a lowermost web, n-2 intermediate webs, and n-1 interfaces of two opposed adjacent contacting surfaces of adjacent webs, whereby a layered stack of webs is formed. Superabsorbent particles are spread such that the particles form a discontinuous layer at one or more of the interfaces between adjacent webs. The layered stack of webs with particles at one or more of the interfaces is crimped between two crimping surfaces having mating z-direction geometrical protrusions and concavities. In describing the crimping surfaces as having mating z-direction geometrical protrusions and concavities, it is sufficient that where one of the crimping surfaces has a protrusion, the other surface has a concavity such that there is some clearance around substantially the entire surface of the protrusion. It is not necessary that the protrusion and concavity have matching geometries. The crimping surfaces need intermesh only sufficiently such that they impart multiple z-direction protrusions and concavities to the layered stack of webs. It is preferable that the crimping surfaces intermesh sufficiently such that they cause opposed adjacent surfaces of webs at each interface to be substantially entirely in contact over the surface areas of the interface, except where particles are present between the opposed adjacent surfaces.

It is preferred that the crimping surfaces impart multiple z-direction protrusions and concavities to the layered stack of webs without producing highly compacted areas in the layered stack of webs. It is desirable to avoid such highly compacted areas because, as described hereinbefore, any particles compressed in such highly compacted areas will not be free to swell in a substantially unconstrained manner. Also, the void volume of the fibrous materials in highly compacted areas is greatly reduced so that the ability of the fibrous materials to temporarily absorb gushes of fluid in such areas is impaired.

Figure 6:
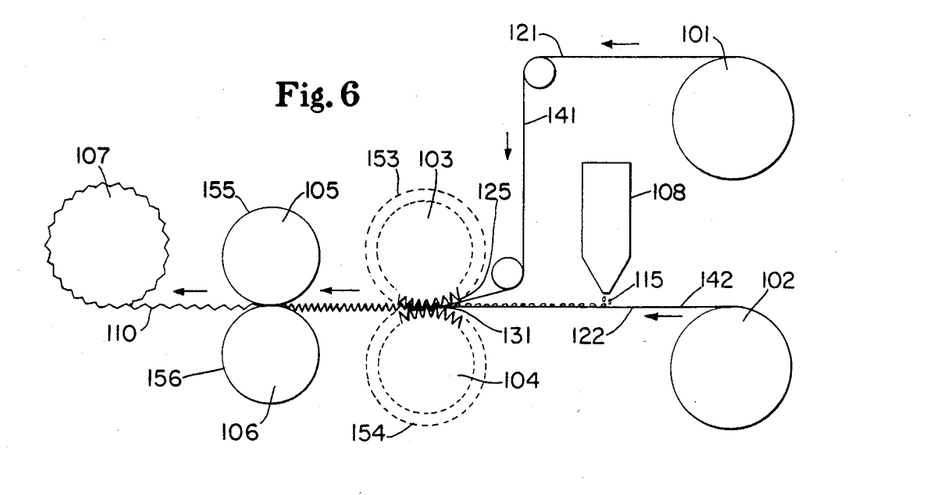
FIG. 6 is a schematic view of a process for producing a layered absorbent structure according to the present invention.

An exemplary process of the present invention for producing layered absorbent structures is shown schematically in FIG. 6. Two substantially planar webs of absorbent tissue 121 and 122 are fed to the process from storage rolls 101 and 102, respectively. Superabsorbent particles 115 are spread from container 108 preferably such that particles 115 form a substantially evenly distributed, discontinuous layer on surface 142 of web 122. Spreading of particles 115 can be done, for example, by hand, sifting, or other mechanical means which achieves the desired even, discontinuous distribution of particles 115.

Webs 121 and 122 are layered such that there is interface 131 between webs 121 and 122 with surface 141 of web 121 and surface 142 of web 122 being opposed adjacent contacting surfaces. Layered webs 121 and 122 with particles 115 at interface 131 between opposed adjacent surfaces 141 of web 121 and 142 of web 122 form layered stack of webs 125 which is fed between crimping rolls 103 and 104. Crimping rolls 103 and 104 have outer cylindrical surfaces which are crimping surfaces 153 and 154, respectively, having mating z-direction geometrical protrusions and concavities. Layered stack of webs 125 is crimped between crimping rolls 103 and 104 thus producing layered absorbent structure 110 having multiple z-direction protrusions and concavities.

Figure 7:
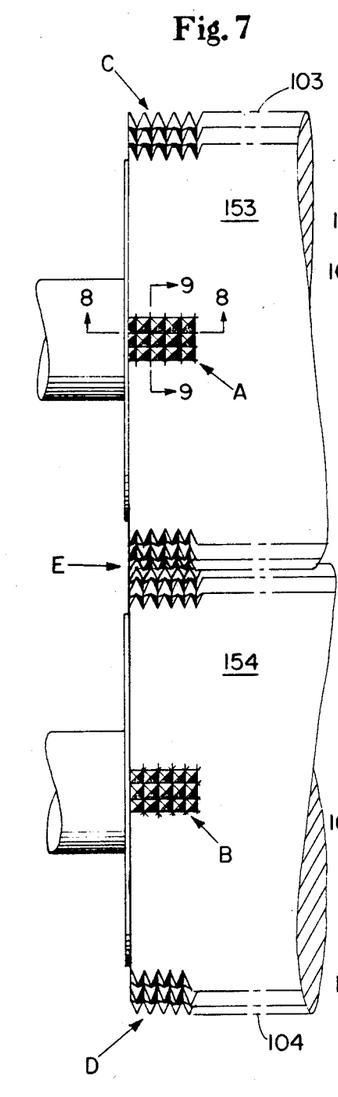
FIG. 7 is a fragmentary, schematic view of the crimping rolls used to produce a layered absorbent structure in the process shown in FIG. 6.

FIG. 7 is a more detailed view of exemplary pair of crimping rolls 103 and 104 which can be used in a preferred process for producing layered absorbent structures of the present invention. Outer cylindrical crimping surfaces 153 and 154 of crimping rolls 103 and 104, respectively, have multiple identical z-direction protrusions. For crimping surfaces 153 and 154, the z-direction is the direction perpendicular to a plane tangent to the cylindrical surface of crimping rolls 103 and 104, respectively. The protrusions of crimping surfaces 153 and 154 are all substantially square-based pyramids. Each square-based pyramid of crimping surface 153 meshes with crimping surface 154 substantially centered among four such pyramids on crimping surface 154; therefore, the mating z-direction concavities in both crimping surfaces 153 and 154 are these depressions among the pyramids of the respective crimping surfaces. These concavities are not impressions of square-based pyramids; this illustrates that the protrusions and concavities need not have the same (but inversed) geometric shape. Areas A and B of FIG. 7 provide schematic plan views of crimping surfaces 153 and 154, respectively. Areas C and D of FIG. 7 provide schematic elevation views of crimping surfaces 153 and 154 respectively. Area E of FIG. 7 provides a schematic elevation view of the intermeshing of crimping surfaces 153 and 154.

Figure 8:
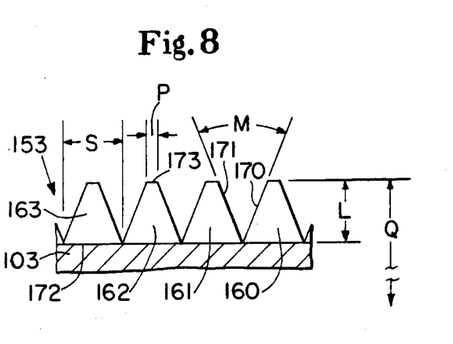
FIG. 8 is a fragmentary, schematic, cross-sectional view of the protrusions and concavities of a crimping roll of FIG. 7 taken along line 8—8.

FIG. 8 is a fragmentary, enlarged, cross-sectional, schematic view of the protrusions of crimping surface 153 taken along Line 8—8 of FIG. 7. Protrusions 160, 161, 162 and 163 are typically square-based pyramids all having substantially the same dimensions. Protrusions 160, 161, 162 and 163 are preferably truncated to remove the sharp pyramid point from each of the protrusions; this reduces tearing of webs of tissue crimped by crimping rolls 103 and 104. In fact, any or all edges of protrusions 160, 161, 162 and 163 may be rounded or smoothed to reduce tearing of webs during crimping. Angle M between adjacent sides 170 of protrusion 160 and 171 of protrusion 161 is typically 45°. z-Direction height L between base 172 and tip 173 of protrusion 160 is typically 2.77 mm. Width P of square, flat tip 173 of protrusion 162 is typically 0.25 mm. Height L may be less and width P may be greater (e.g. 0.5 mm or greater) if more truncation of protrusions 160, 161, 162 and 163 is desired to further reduce tearing of webs of tissue during crimping. Width S of protrusion 162 at base 172 is typically 2.54 mm. Diameter Q of crimping roll 103 from protrusion tips to protrusion tips is typically 94.6 mm.

Figure 9:
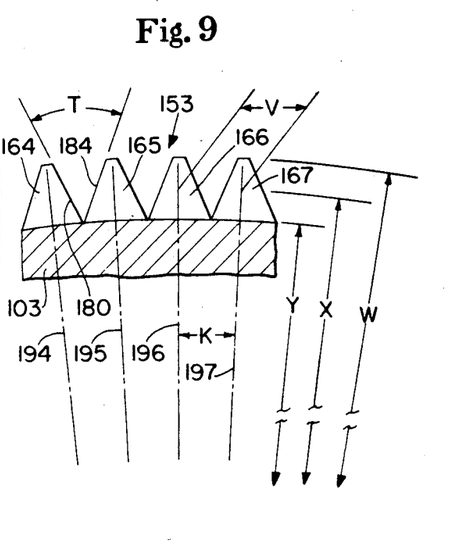
FIG. 9 is a fragmentary, schematic, cross-sectional view of the protrusions and concavities of a crimping roll of FIG. 7 taken along line 9—9.

FIG. 9 is a fragmentary enlarged cross-sectional schematic view of crimping surface 153 of crimping roll 103 taken along Line 9—9 of FIG. 7. Protrusions 164, 165, 166 and 167 are typically square-based truncated pyramids all having the same dimensions. Angle T between surfaces 180 of protrusion 164 and 184 of protrusion 165 is typically 45°. As viewed in FIG. 9, protrusions 164, 165, 166 and 167 are symmetrically centered on center lines 194, 195, 196 and 197, respectively; these center lines project radially from the center of crimping roll 103. The angle between center lines 196 and 197 of adjacent protrusions 166 and 167, respectively, is typically 3.158°. Diameter W of crimping roll 103 from protrusion tips to protrusion tips is typically 94.6 mm; diameter Y from protrusion bases to protrusion bases is typically 89.1 mm; and diameter X between nominal centers of the protrusions is typically 92.2 mm. Distance V between adjacent protrusions 166 and 167 at their nominal center line is typically 2.54 mm.

As stated hereinbefore, it is preferred that the opposed adjacent surfaces of adjacent webs of preferred layered absorbent structures of the present invention are frangibly bonded substantially entirely due to the intermeshing of the z-direction protrusions of one surface with z-direction concavities of its opposed adjacent surface. The strength of the bond between such opposed adjacent surfaces will depend on factors such as the number and shape of the intermeshing z-direction protrusions and concavities, the surface properties of the webs of fibrous materials, and the density of the absorbent particles at the interfaces between the webs.

In general, a greater number of such protrusions and concavities having a given height, or a higher height of such protrusions having a given base width will result in a stronger bond between opposed adjacent surfaces of adjacent webs. For the preferred crimping surfaces 153 and 154 of crimping rolls 103 and 104 shown in FIGS 7, 8 and 9, there are about 16 protrusions per square centimeter of crimping surface. Using the length of one side of the square base of the pyramidal-shaped protrusions as the base width of the protrusion, the height to base width ratio of the protrusions of crimping surfaces 153 and 154 is about 1.1:1.

Although the configuration of crimping surfaces 153 and 154 are preferred, an almost infinite variety of protrusion and concavity shapes and patterns could be provided on crimping surfaces in order to produce the necessary intermeshing z-direction protrusions and concavities in the preferred layered absorbent structures of the present invention. It is preferred that at least one of such crimping surfaces have from about 10 to about 50 protrusions per square centimeter, more preferably from about 15 to about 25 protrusions per square centimeter. It is preferred that the z-direction height of such protrusions be from about 1 mm to about 5 mm, more preferably from about 2 mm to about 3 mm. It is preferred that such protrusions taper substantially entirely from their base to their tip. The preferred protrusions are pyramidal or conical shaped; however, a large variety of shapes which would be suitable can readily be conceived by a skilled artisan. Processes of the present invention are not limited to any particular size or shape of protrusion or concavity.

Crimping surfaces 153 and 154 of rolls 103 and 104 have protrusions which are all substantially identical. Although this type of pattern is preferred, it would be possible to have a wide variety of protrusion and concavity shapes on such crimping surfaces. It is also preferred, but not necessary, that both crimping surfaces have both z-direction protrusions and z-direction concavities.

Figure 14:
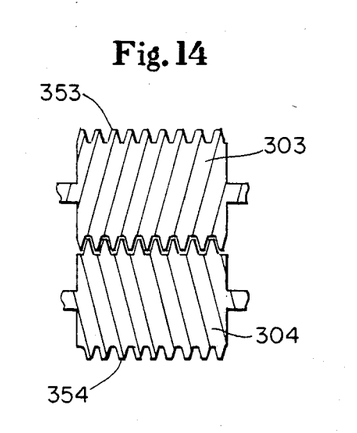
FIG. 14 is a schematic cross-sectional view of another pair of crimping rolls that can be used to produce layered absorbent structures of the present invention.

Crimping surfaces 153 and 154 of rolls 103 and 104 have discreet pyramidal shaped z-direction protrusions. Z-direction protrusions and concavities could be imparted to preferred layered absorbent structures of the present invention by less discreet protrusions on the crimping surfaces. An example are the crimping surfaces 353 and 354 of ring rolls 303 and 304 shown in FIG. 14. The z-direction protrusions and concavities imparted to a layered absorbent structure of the present invention by ring rolls 303 and 304 would be substantially continuous ridges and troughs.

Crimping surfaces 153 and 154 of rolls 103 and 104 are preferably made of a rigid material such as hardened steel.

The pressure needed between crimping rolls 103 and 104 of FIG. 6 must be great enough to impart sufficient z-direction protrusions and concavities to layered stack of webs 125, but should not be so great as to cause heavy compaction of the stack of webs. Such pressure is preferably great enough to crimp layered stack 125 sufficiently such that opposed adjacent surfaces 141 of web 121 and 142 of web 122 are substantially entirely in contact over the surface area of interfaces 131 and are bonded by fiber entanglement, except where particles 115 are between surfaces 141 and 142, so that particles 115 are immobilized substantially entirely by fiber entrapment; but little enough such that surfaces 141 and 142 are frangibly bonded such that, if structure 110 is subsequently wetted, particles 115 are able to swell without substantial constraint of the swelling by the entrapping fibers. The pressure needed to achieve the desired structure depends on factors such as the number and thickness of webs of fibrous materials and the crimping pattern of the crimping rolls. It has been found that it is often desirable to set a certain minimum gap between crimping rolls 103 and 104 to insure that overcompaction of layered absorbent structure 110 does not occur. This is accomplished by moving crimping rolls 103 and 104 together until crimping surfaces 153 and 154 are in contact, and then moving rolls 103 and 104 apart the desired gap distance.

It has been found that while most of particles 115 are immobilized in layered absorbent structure 110 emanating from crimping rolls 103 and 104, the ability of structure 110 to hold the particles in place can sometimes be disrupted by handling and flexing of structure 110. When this occurs, particles 115 move between webs of fibrous materials 121 and 122 and may tend to cluster together so that they are no longer evenly distributed at interface 131. This has been found to occur particularly when the protrusions and concavities imparted by crimping rolls 103 and 104 are larger and spaced further apart. It has been found that particles 115 can be stabilized in their evenly distributed positions at interface 131 by passing layered absorbent structure 110 between compression rolls 105 and 106 which have substantially smooth cylindrical surfaces 155 and 156, respectively. Smooth compression rolls 105 and 106 preferably have compression surfaces 155 and 156 made of rigid material such as hardened steel. The pressure between smooth compression rolls 105 and 106 is limited so that the configuration of crimped structure 110 is not greatly altered; however, the crimping pattern in layered absorbent structure 110 is smoothed out somewhat and particles 115 are affixed more securely at interface 131 by compressing structure 110 between rolls 105 and 106.

Because of the substantial distortion that stack of webs 125 undergoes between crimping surfaces 153 and 154 of crimping rolls 103 and 104, some separation of fibers and/or tearing of the webs of fibrous materials almost inevitably occurs. It has also been found that by passing crimped layered absorbent structure 110 emanating from between crimping rolls 103 and 104 between compression rolls 105 and 106, holes in webs of fibrous material 121 and 122 are closed somewhat so that superabsorbent polymer particles 115 are less likely to escape from structure 110.

The pressure between smooth rolls 105 and 106 must be kept low to avoid excessive flattening of the protrusions and concavities imparted by crimping rolls 103 and 104, and also to avoid substantial compaction of webs of fibrous materials 121 and 122. Such compaction could impair the swelling of particles 115 when they are absorbing fluid, and would decrease the void volume of layered absorbent structure 110, thus decreasing its capacity to handle gushes of fluid. Smooth rolls 105 and 106 are each typically 9.2 cm in diameter. The pressure at the nip of smooth compression rolls 105 and 106 is preferably from about 5 kg/cm of web width to about 50 kg/cm of web width, more preferably from about 15 kg/cm of web width to about 25 kg/cm of web width.

Layered absorbent structure 110 may be taken directly from rolls 105, 106 for conversion into products such as disposable diapers, catamenial devices, and the like. In FIG. 6, it is shown that layered absorbent structure 110 is accumulated on storage roll 107.

Layered absorbent structures of the present invention having multiple webs of fibrous materials can be produced by several alternative means. In a process similar to that shown in FIG. 6, several webs of fibrous material could have superabsorbent particles spread on them; the several webs of fibrous material could then be layered and passed between one set of crimping rolls such as rolls 103 and 104, thus producing a multi-layered absorbent structure with one crimping step.

Figure 10:
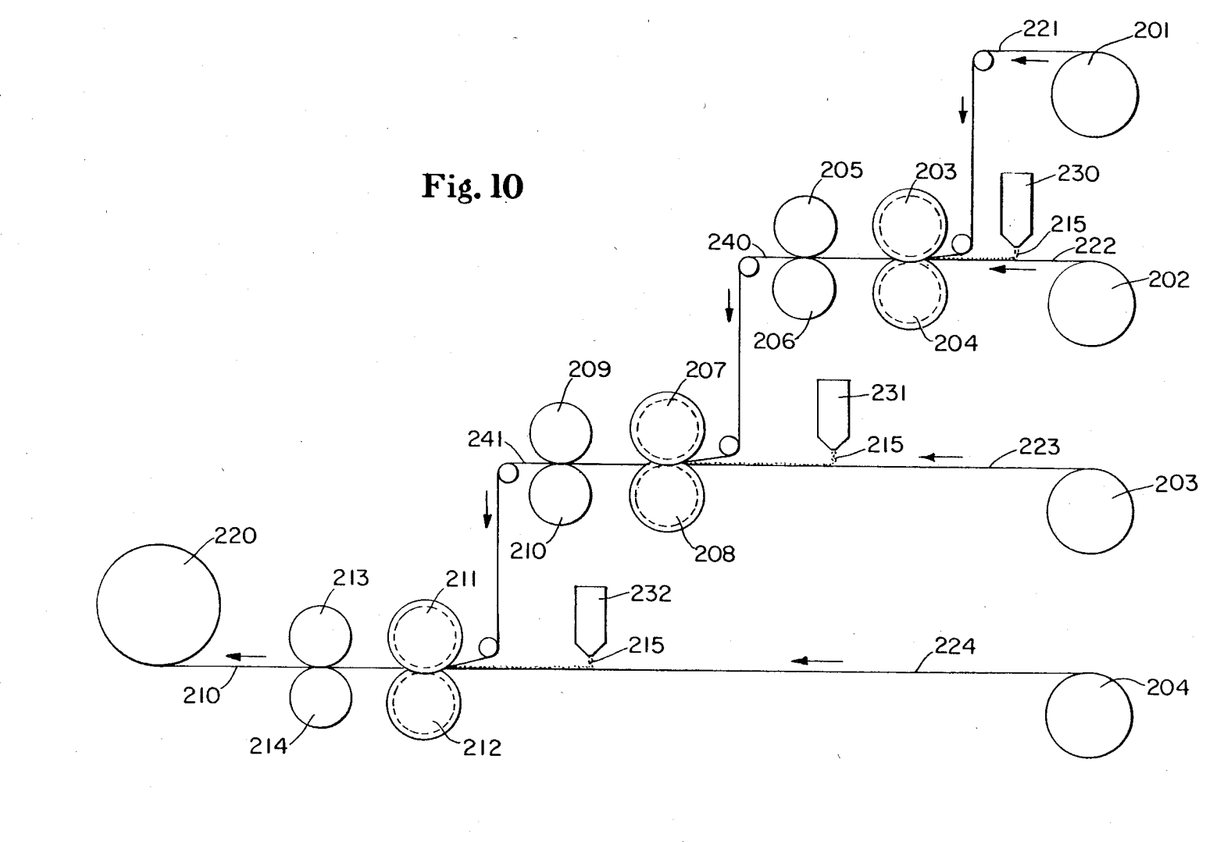
FIG. 10 is a schematic view of a process for producing a multi-layered absorbent structure according to the present invention.

An alternative process for producing a multi-layered absorbent structure of the present invention is shown in FIG. 10. Webs of fibrous materials 221, 222, 223 and 224 are fed to the process from storage rolls 201, 202, 203 and 204, respectively. Superabsorbent polymer particles 215 are spread from container 230 on web 222 which is then layered with web 221; the layered webs 221 and 222 are crimped between the crimping surfaces of crimping rolls 203 and 204 and then compressed between smooth compression rolls 205 and 206, thus forming layered structure 240. Superabsorbent polymer particles 215 are spread from container 231 on web 223 which is then layered with layered structure 240 and crimped between the crimping surfaces of crimping rolls 207 and 208 and compressed between smooth rolls 209 and 210, thus forming layered structure 241. Superabsorbent polymer particles 215 are spread from container 232 on web of 224 which is then layered with layered structure 241 and crimped between the crimping surfaces of crimping rolls 211 and 212 and compressed between smooth rolls 213 and 214, thus forming layered absorbent structure 210. Layered absorbent structure 210 is accumulated on storage roll 220.

Figure 11:
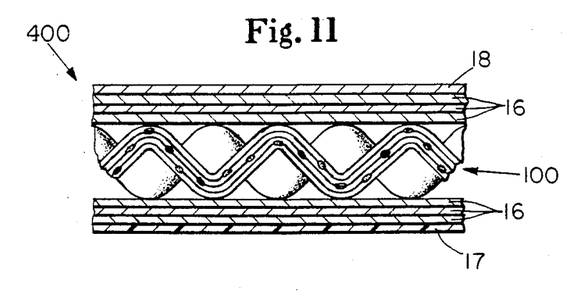
FIG. 11 is a fragmentary, enlarged, cross-sectional, schematic elevation view of a disposable diaper made according to the present invention.
Figure 12:
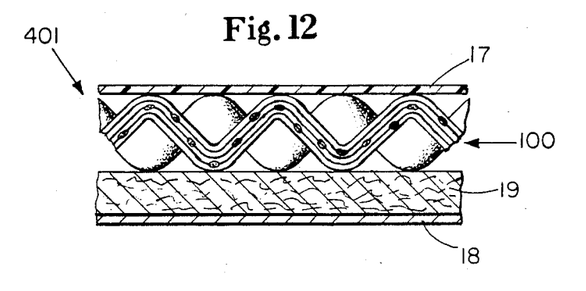
FIG. 12 is a fragmentary, enlarged, cross-sectional, schematic elevation view of another disposable diaper made according to the present invention.
Figure 13:
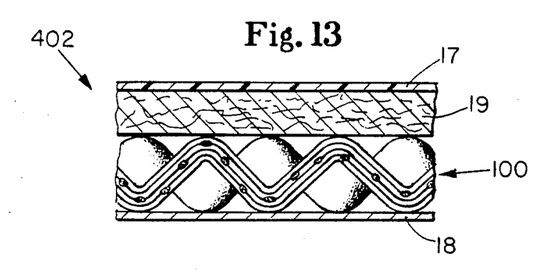
FIG. 13 is a fragmentary, enlarged, cross-sectional, schematic elevation view of another disposable diaper made according to the present invention.

The layered absorbent structures of the present invention as described hereinbefore, can be used as absorbent cores in disposable diapers, disposable incontinent briefs, catamenial devices, bandages, and the like. An almost infinite variety of combinations of the layered absorbent structures of the present invention with other materials is envisioned for such products. Such products may use layered absorbent structures of the present invention layered singly or multiply, with or without other absorbent or non-absorbent materials. FIGS. 11, 12 and 13 show fragmentary, enlarged, cross-sectional, schematic views of exemplary disposable diapers utilizing layered absorbent structures of the present invention. Such disposable diaper structures preferably comprise a fluid-permeable topsheet, a substantially fluid impermeable backsheet, and a layered absorbent structure of the present invention between the topsheet and the backsheet.

A preferred disposable diaper structure comprises one or more layers of absorbent paper between the layered absorbent structure of the present invention and the topsheet, and between the layered absorbent structure and the backsheet. In FIG. 11, disposable diaper struture 400 has layered absorbent structure 100 such as that shown in FIG. 3 with three layers of absorbent tissues 16 on each side of layered absorbent structure 100. The basis weight of layered absorbent structure 100 is about 100 g/m²; each layer of absorbent tissue 16 has a basis weight of about 18 g/m². One surface layer of diaper structure 400 is backsheet 17 which is an impermeable material; the other surface layer 18 of diaper structure 400 is a fluid-permeable topsheet.

Other preferred disposable diaper structures include the use of layered absorbent structures of the present invention as inserts to provide additional absorption capacity in conventional disposable diapers. Such diaper structures preferably comprise an absorbent fibrous batt between the layered absorbent structure and the topsheet, or between the layered absorbent structure and the backsheet. In FIG. 12, disposable diaper structure 401 has layered absorbent structure 100 adjacent backsheet 17 which is a thermoplastic film. Between topsheet 18 and layered absorbent structure 100 is absorbent air felt batt 19 which is conventionally used as an absorbent core for disposable diapers. When used as an inert in a conventional diaper structure, layered absorbent structure 100 may be included only in the central portion of the diaper where there is the greatest need for additional absorption capacity. The basis weight of layered absorbent structure 100 is typically about 18 g/m² and of batt 19 is typically about 300 g/m². The density of batt 19 is preferably from about 0.05 g/cm³ to about 0.35 g/cm³. In FIG. 13, disposable diaper structure 402 has layered absorbent structure 100 adjacent topsheet 18 and airfelt batt 19 between backsheet 17 and layered absorbent structure 100.

The following examples will illustrate the invention, but are not intended to be limiting thereof in any way.

EXAMPLE 1

A layered absorbent structure of the present invention was produced using four plies of conventional tissue comprised of ⅓ northern softwood, ⅓ souther softwood, and ⅓ hardwood, available commercially from Lincoln Pulp & Paper Company, Inc., Lincoln, Maine. The tissue had a basis weight of 17 g/m² and a thickness of 0.26 mm. A layer of superabsorbent polymer particles was substantially evenly spread at each of the three interfaces between the layers of tissue by hand sifting. The superabsorbent polymer particles used were a starch-polyacrylic acid graft copolymer, Sanwet IM-1000, commercially available from Sanyo Chemical Industries, Kyoto, Japan. The Sanwet IM-1000 particles had the following particle size distribution:

| Particle Size (mm) | Percent (by weight) |
|---|---|
| >0.6 | 15 |
| 0.6–0.4 | 31 |
| 0.4–0.3 | 15 |
| 0.3–0.15 | 25 |
| 0.15–0.045 | 11 |
| <0.045 | 3 |

The particles were spread at an average density of 0.0011 g/cm² at each of the three interfaces between the tissue layers. The layered stack of tissue plies with particles between was then fed between crimping rolls 103 and 104 shown in FIG. 7. A minimum gap of 0.43 mm between rolls 103 and 104 was set, and a loading pressure of 19 kg/cm of structure width was used. The layered absorbent structure thus produced was then fed between smooth compression rolls 105 and 106 shown in FIG. 6 under a pressure load of 18 kg/cm of structure width. The resulting layered absorbent structure was used as an absorbent core in disposable diaper structure 400 shown in FIG. 11.

EXAMPLE 2

A layered absorbent structure of the present invention was made using two plies of absorbent tissue similar to that used in Example 1 except the tissue has a basis weight of 18 g/m² and a thickness of 0.29 mm. A layer of Sanwet IM-1000 particles was substantially evenly spread between the tissue layers at an average density of 0.0031 g/cm² by hand sifting. The layered stack of tissue plies with Sanwet particles between the tissue plies was fed between crimping rolls similar to rolls 103 and 104 shown in FIGS. 6 and 7. The crimping rolls used had 40 pyramidal shaped protrusions per cm²; the protrusions had the same pattern as crimping rolls 103 and 104 and the protrusions had the same height to base width ratio as those of rolls 103 and 104. The minimum gap between the crimping rolls was set at 1.12 mm. The resulting layered absorbent structure was used as an insert in the absorbent core of disposable diaper structures such as 401 and 402 shown in FIGS. 12 and 13.

EXAMPLE 3

A layered absorbent structure of the present invention was produced using four plies of soft, bulky absorbent tissue made according to the teachings of U.S. Pat. No. 3,301,746 issued to Sanford & Sisson on Jan. 31, 1967, the specification of which is incorporated herein by reference. The tissue had a basis weight of 15 g/m² and a thickness of 0.18 mm. A layer of superabsorbent polymer particles was substantially evenly spread at each of the three interfaces between the layers of tissue by hand sifting. The superabsorbent polymer particles used were an acrylic acid polymer, Aquakeep, commercially available from Seitetsu Kagaku Company Ltd., Osaka, Japan. The Aquakeep particles had the following particle size distribution:

| Particle size (mm) | Percent (by weight) |
|---|---|
| >0.6 | 5 |
| 0.6–0.42 | 9 |
| 0.42–0.3 | 27 |
| 0.3–0.18 | 50 |
| 0.18–0.045 | 9 |

The particles were spread at an average density of 0.0012 g/cm² at each of the three interfaces between the tissue layers. The layered stack of tissue plies with particles between was fed between crimping rolls 103 and 104 and smooth compression rolls 105 and 106 under the same conditions as the structure of Example 1.

EXAMPLE 4

A layered absorbent structure of the present invention was produced using six plies of a soft, bulky absorbent tissue similar to that used in Example 3 except that the tissue had a basis weight of 18 g/m² and a thickness of 0.29 mm. A layer of superabsorbent polymer particles was substantially evenly spread at each of the five interfaces between the layers of tissue by hand sifting. The superabsorbent polymer particles used were the same as used in Example 3. The particles were spread at an average density of 0.0012 g/cm² at each of the five interfaces between the tissue layers. The layered stack of tissue plies with particles between was then crimped between flat plates having substantially the same pyramidal protrusion patterns as crimping rolls 103 and 104 at a pressure of 7 kg/cm² for 30 seconds. The crimped struture was then compressed between flat plates at a pressure of 4 kg/cm² for 30 seconds.

EXAMPLE 5

A layered absorbent structure of the present invention was produced using four plies of tissue similar to that used in Example 3 except that the tissue had a basis weight of 36 g/m² and a thickness of 0.51 mm. A layer of superabsorbent polymer particles was substantially evenly spread at each of the three interfaces between the layers of tissue by hand sifting. The superabsorbent polymer particles used were Sanwet IM-1000 particles. The particles were spread at an average density of 0.0011 g/cm² at each of the three interfaces between the tissue layers. The layered stack of tissue plies with particles between was then fed between crimping rolls 103 and 104 and smooth compression rolls 105 and 106 under the same conditions as for Example 1 except that the minimum gap between rolls 103 and 104 was set at 0.76 mm.

EXAMPLE 6

A layered absorbent structure of the present invention was made using three plies of absorbent tissue similar to that used in Example 1 except that the tissue has a basis weight of 15 g/m² and a thickness of 0.18 mm. A layer of Sanwet IM-1000 particles was substantially evenly spread between two of the tissue layers at an average density of 0.0012 g/cm² by hand sifting. The layered stack of two tissue plies with Sanwet particles between the tissue plies was fed between crimping rolls 103 and 104 and smooth compression rolls 105 and 106 under the same conditions as for Example 1. A layer of Sanwet IM-1000 particles was substantially evenly spread between the third tissue layer and the two-tissue layer laminate previously produced. The particles were spread at an average density of 0.0012 g/cm². The resulting layered stack was then fed between crimping rolls 103 and 104 and smooth compression rolls 105 and 106 under the same conditions as for Example 1. The resulting layered absorbent structure was used as an inert in the absorbent core of disposable diaper structures such as 401 and 402 shown in FIGS. 12 and 13.

While particular embodiments of the invention have been illustrated and described, it would be obvious to those skilled in the art that various changes and modifications can be made without departing from the spirit and scope of the invention. In particular, it is contemplated that a wide variety of products utilizing the layered absorbent structures of the present invention in absorbent cores for products such as disposable diapers, catamenial devices, bandages, and the like, can be achieved by combining such layered absorbent structures with a variety of other materials. It is intended to cover, in the appended claims all such modifications and contemplated uses of such layered absorbent strutures.

What is claimed is:

1. A layered absorbent structure of substantially uniform overall density, said structure having an upper surface and a lower surface, said structure comprising:
   (a) n webs of fibrous materials, n being an integer of two or more, said webs being layered such that there is an uppermost web, a lowermost web, n−2 intermediate webs, and n−1 interfaces of two opposed adjacent contacting surfaces of adjacent webs, each of said interfaces having a surface area; and
   (b) discretely spaced absorbent particles forming a discontinuous layer at one or more of said interfaces;
   said opposed adjacent contacting surfaces, at each said interface where said particles are present, being substantially entirely frangibly bonded to one another by fiber entanglement at substantially all points of contact between said contacting surfaces without creating discrete areas of densification in said webs of fibrous materials, said frangible bonding of said opposed adjacent contacting surfaces by fiber entanglement being strong enough to keep said discretely spaced particles immobilized at said interface(s) while said layered absorbent structure remains dry, yet weak enough to separate and allow substantially unconstrained expansion of said absorbent particles when said layered absorbent structure is wetted by an aqueous fluid.

2. The structure of claim 1 wherein said discretely spaced absorbent particles are substantially evenly distributed over said surface area of each said interface where said particles are present.

3. The structure of claim 2 wherein said absorbent particles are superabsorbent polymer particles which are substantially dry.

4. The structure of claim 3 wherein each of said fibrous webs exhibits a substantially uniform wicking characteristic across its surface, whereby if said structure is subsequently wetted by an aqueous fluid, each of said fibrous webs rapidly wicks said fluid in a substantially uniform manner across its surface to said discretely spaced absorbent particles, which particles absorb said fluid, swell and become substantially saturated in a substantially unconstrained manner.

5. The structure of claim 4 wherein said absorbent particles cover less than 90% of said surface area of each of said interfaces when they become substantially saturated.

6. The structure of claim 4 wherein said opposed adjacent surfaces of said adjacent webs, at each said interface where particles are present, are substantially entirely in contact over substantially all of said surface area of said interface except where said absorbent particles are present between said opposed adjacent surfaces and wherein overcoming said frangible bonding between said opposed adjacent surfaces of said adjacent webs by peeling involves at least a degree of sliding of one of said adjacent surfaces across the other.

7. A layered absorbent structure of substantially uniform overall density, said structure having an upper surface and a lower surface, said structure comprising:
   (a) n webs of fibrous materials, n being an integer of two or more, each of said webs having two substantially parallel surfaces, said webs being layered such that there is an uppermost web, a lowermost web, n−2 intermediate webs, and n−1 interfaces of two opposed adjacent contacting surfaces of adjacent webs, each of said interfaces having a surface area; each of said webs having multiple z-direction protrusions in one or both of its surfaces, each said protrusion having a corresponding z-direction concavity in the other surface of said web; where at each said interface, each z-direction protrusion of an adjacent surface intermeshes with a concavity of its opposed adjacent surface; and (b) discretely spaced absorbent particles forming a discontinuous layer at one or more of said interfaces;

said opposed adjacent contacting surfaces, at each said interface where said particles are present, being substantially entirely frangibly bonded to one another by fiber entanglement at substantially all points of contact between said contacting surfaces without creating discrete areas of densification in said webs of fibrous material, said frangible bonding of said opposed adjacent contacting surfaces by fiber entanglement being strong enough to keep said discretely spaced particles immobilized at said interface(s) while said layered absorbent structure remains dry, yet weak enough to separate and allow substantially unconstrained expansion of said absorbent particles when said layered absorbent structure is wetted by an aqueous fluid.

8. The structure of claim 7 wherein said opposed adjacent surfaces of said adjacent webs at said interface(s) where said particles are present are substantially entirely frangibly bonded by fiber entanglement between said contacting surfaces due to said intermeshing of said z-direction protrusions with said z-direction concavities.

9. The structure of claim 8 wherein said discretely spaced particles are substantially evenly distributed over said surface area of each said interface where said particles are present, and wherein said particles are immobilized within said structure substantially entirely by fiber entrapment.

10. The structure of claim 9 wherein said absorbent particles are superabsorbent polymer particles which are substantially dry.

11. The structure of claim 10 wherein said opposed adjacent surfaces of said adjacent webs at each said interface where particles are present are substantially entirely in contact over substantially all of said surface area of said interface except where said absorbent particles are present between said opposed adjacent surfaces and wherein overcoming said frangible bonding between said opposed adjacent surfaces of said adjacent webs by peeling involves at least a degree of sliding of one of said adjacent surfaces across the other.

12. The structure of claim 10 wherein said particles cover no more than 50% of said surface area of each of said interfaces.

13. The structure of claim 10 wherein about 90% (by weight) or more of said particles have an average diameter of from about 0.05 mm to about 1.0 mm.

14. The structure of claim 10 wherein one or both of said surfaces of each said web has from about 10 to about 50 protrusions per square centimeter.

15. The structure of claim 10 wherein each of said fibrous webs exhibits a substantially uniform wicking characteristic across its surface, whereby if said structure is subsequently wetted by an aqueous fluid, each of said fibrous webs rapidly wicks said fluid in a substantially uniform manner across its surface to said discretely spaced absorbent particles, which particles absorb said fluid, swell and become substantially saturated in a substantially unconstrained manner.

16. The structure of claim 15 wherein said absorbent particles cover less than 100% of said surface area of each of said interfaces when they become substantially saturated.

17. The structure of claim 16 wherein said particles have a water absorption capacity of 30 times their dry weight or more.

18. The structure of claim 16 wherein said superabsorbent polymer comprises saponified starch-polyacrylonitrile graft copolymers, starch-polyacrylic acid graft copolymers, crosslinked/grafted cellulose, saponified vinyl acetate-acrylic acid copolymers, starch grafted polyvinyl acetate, acrylic acid polymers, or crosslinked polyethylene oxide, or mixtures thereof.

19. The structure of claim 10 wherein said webs are absorbent papers.

20. The structure of claim 14 wherein said webs are absorbent tissues.

21. The structure of claim 20 wherein each of said webs has a basis weight of from about 15 $g/m^2$ to about 40 $g/m^2$.

22. The structure of claim 10 wherein said webs are absorbent tissues each having a basis weight of from about 10 $g/m^2$ to about 100 $g/m^2$.

23. The structure of claim 10 wherein n is from 2 to about 12.

24. The structure of claim 20 wherein n is from 2 to about 12.

25. The structure of claim 21 wherein n is from 2 to about 5.

26. A disposable diaper structure comprising:
(a) a fluid-permeable topsheet;
(b) a substantially fluid impermeable backsheet; and
(c) a layered absorbent structure of substantially uniform overall density, said structure having an upper surface and a lower surface, said structure comprising:

(I) n webs of fibrous materials, n being an integer of two or more, each of said webs having two substantially parallel surfaces, said webs being layered such that there is an uppermost web, a lowermost web, n−2 intermediate webs, and n−1 interfaces of two opposed adjacent contacting surfaces of adjacent webs, each of said interfaces having a surface area; each of said webs having multiple z-direction protrusions in one or both of its surfaces, each said protrusion having a corresponding z-direction concavity in the other surface of said web; where at each said interface, each z-direction protrusion of an adjacent surface intermeshes with a concavity of its opposed adjacent surface;

(II) discretely spaced absorbent particles forming a discontinuous layer at one or more of said interfaces, said opposed adjacent contacting surfaces, at each said interface where said particles are present, being substantially entirely frangibly bonded to one another by fiber entanglement at substantially all points of contact between said contacting surfaces without creating discrete areas of densification in said webs of fibrous material, said frangible bonding of said opposed adjacent contacting surfaces by fiber entanglement being strong enough to keep said discretely spaced particles immobilized at said interface(s) while said layered absorbent structure remains dry, yet weak enough to separate and allow substantially unconstrained expansion of said absorbent particles when said layered absorbent structure is wetted by an aqueous fluid;

said layered absorbent structure being between said topsheet and said backsheet.

27. The disposable diaper structure of claim 26 wherein said absorbent particles are superabsorbent polymer particles.

28. The disposable diaper structure of claim 27 wherein said diaper structure also comprises:
(d) one or more layers of absorbent paper between said layered absorbent structure and said topsheet, and between said layered absorbent structure and said backsheet.

29. The disposable diaper structure of claim 27 wherein said diaper structure also comprises:
(d) an absorbent fibrous batt between said layered absorbent structure and said topsheet.

30. The disposable diaper structure of claim 27 wherein said diaper structure also comprises:
(d) an absorbent fibrous batt between said layered absorbent structure and said backsheet.

31. The disposable diaper structure of claim 29 wherein the density of said fibrous batt is from about 0.05 g/cm$^2$ to about 0.35 g/cm$^3$.

32. The disposable diaper structure of claim 30 wherein the density of said fibrous batt is from about 0.05 g/cm$^2$ to about 0.35 g/cm$^3$.

* * * * *